US00PP16480P3

(12) United States Plant Patent

Weber et al.

(10) Patent No.: US PP16,480 P3
(45) Date of Patent: Apr. 25, 2006

(54) STRAWBERRY PLANT NAMED 'L'AMOUR'

(50) Latin Name: *Fragaria×ananassa*
Varietal Denomination: L'Amour

(75) Inventors: Courtney A. Weber, Geneva, NY (US); John C. Sanford, Livonia, NY (US); Kevin E. Maloney, Phelps, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 131 days.

(21) Appl. No.: 10/872,694

(22) Filed: Jun. 21, 2004

(65) Prior Publication Data

US 2005/0283868 P1 Dec. 22, 2005

(51) Int. Cl.
*A01H 5/00* (2006.01)

(52) U.S. Cl. ..... Plt./208
(58) Field of Classification Search ..... Plt./208
See application file for complete search history.

(56) References Cited

PUBLICATIONS

Varieties [online] [retrieved on Jan. 26, 2005]. Retrieved from the Internet: <http://www.agraria.it/isf/attivit/fragola/ishs/varieties.htm#c>.*

* cited by examiner

*Primary Examiner*—Anne Marie Grunberg
*Assistant Examiner*—June Hwu
(74) *Attorney, Agent, or Firm*—Jondle & Associates, P.C.

(57) ABSTRACT

This invention relates to a new and distinct June-bearing cultivar of strawberry plant named 'L'Amour' primarily adapted to the growing conditions of west central New York and other regions of similar climate. The new cultivar is primarily characterized by strong vigor, large flowers, longer than broad fruit, conical fruit shape, uniformity in shape between primary and secondary fruit, bright red fruit color, glossy skin, very firm fruit flesh, large reflexed calyx, and long pedicels and fruiting trusses.

3 Drawing Sheets

Genus and species: *Fragaria×ananassa* Duch.
Cultivar denomination: 'L'Amour'.

SUMMARY OF THE INVENTION

The present invention relates to a new and distinct June-bearing (short day responsive) strawberry cultivar designated as 'L'Amour'. The cultivar is botanically known as *Fragaria×ananassa* Duch. The new and distinct cultivar of strawberry originated from a hand-pollinated cross of New York Selection NYUS256 (not patented)×'Cavendish' (U.S. Plant Pat. No. 11,110), made in 1994 at the New York State Agricultural Experiment Station at Geneva, N.Y. NYUS256 is June-bearing with fruit that is dark red, firm fleshed, and conic shaped that ripens later than 'L'Amour'. 'Cavendish' is June-bearing with fruit that is a bright red, wedge shaped, moderately firm fleshed that ripens slightly earlier than 'L'Amour'. Both parents of 'L'Amour' are hybrids of the strawberry genus of the species *Fragaria×ananassa.* Thus, 'L'Amour' is of the species *Fragaria×ananassa.* The seeds resulting from this controlled hybridization were germinated in a greenhouse during the winter of 1994–95. Resulting seedlings were planted in the spring of 1995 in a field on the New York State Agricultural Experiment Station at Geneva, N.Y. The seedlings fruited in the summer of 1996 and one, designated NY1829, was selected for its attractive, large, bright red fruit, strong strawberry flavor, and firm flesh.

During 1996, the original plant selection was propagated asexually by stolons (runners) at Geneva, N.Y. and a test planting of ten plants was established. Subsequently, larger test plantings have been established with asexually multiplied plants at Geneva, N.Y. The new cultivar was then tested over the next several years in the fruiting fields at Geneva, N.Y. Further propagation in South Deerfield, Mass. was completed using tissue culture to produce disease free material for use in further testing. Tissue culture plants were used as mother plants for propagation from stolons. This propagation has demonstrated that the combination of traits disclosed herein as characterizing the new cultivar are fixed and remain true to type through successive generations of asexual reproduction. All propagules of 'L'Amour' have been observed to be true to type in that during all asexual multiplication, the vegetative and fruit characteristics of the original plant have been maintained. All plants planted from dormant crowns or rooted runner tips have fruited after one season of growth in the field.

Test plantings in various locations in New York, Pennsylvania, Ohio, Michigan, and Ontario, Canada have shown this cultivar to be widely adapted to differing soil and climatic conditions. The variety has shown cold hardiness typical to strawberries in a matted row system when covered with straw in the winter, which is standard procedure for this growing region. Fruit of the new cultivar ripens after the cultivar 'Honeoye' (not patented), similar to the cultivar 'Darselect' (U.S. Plant Pat. No. 10,402). and before the cultivar 'Jewel' (U.S. Plant Pat. No. 5,897).

The new cultivar is primarily adapted to the climate and growing conditions of west central N.Y., the upper mid-western U.S., the mid-Atlantic states, and southeastern Canada. This region provides the necessary winter temperatures required for it to produce a strong, vigorous plant and to produce fruit in the summer harvest season from May to July, depending on location.

The following list of traits in combination define the new cultivar as a unique cultivar distinguishing it from other commercial varieties in the region:

1. upright growth habit, strong vigor;
2. moderate leaf gloss, light interveinal blistering, globose leaflets with equal length and width;
3. longer than broad fruit, conical fruit shape, uniform shape between primary and secondary fruit, bright red fruit color and flesh color, very good fruit gloss and flesh firmness;
4. highly reflexed calyx;
5. long pedicels and peduncles with few bracts;
6. early mid-season production with moderate yields; and
7. compact harvest season.

BRIEF DESCRIPTION OF THE PHOTOGRAPHS

The accompanying color photographs show typical specimens of the new cultivar at various stages of development as nearly true as it is possible to make in color reproductions. The depicted plant and plant parts were from the second harvest season, approximately 25 months after planting.

DETAILED BOTANICAL DESCRIPTION OF NEW CULTIVAR

Figure 1:
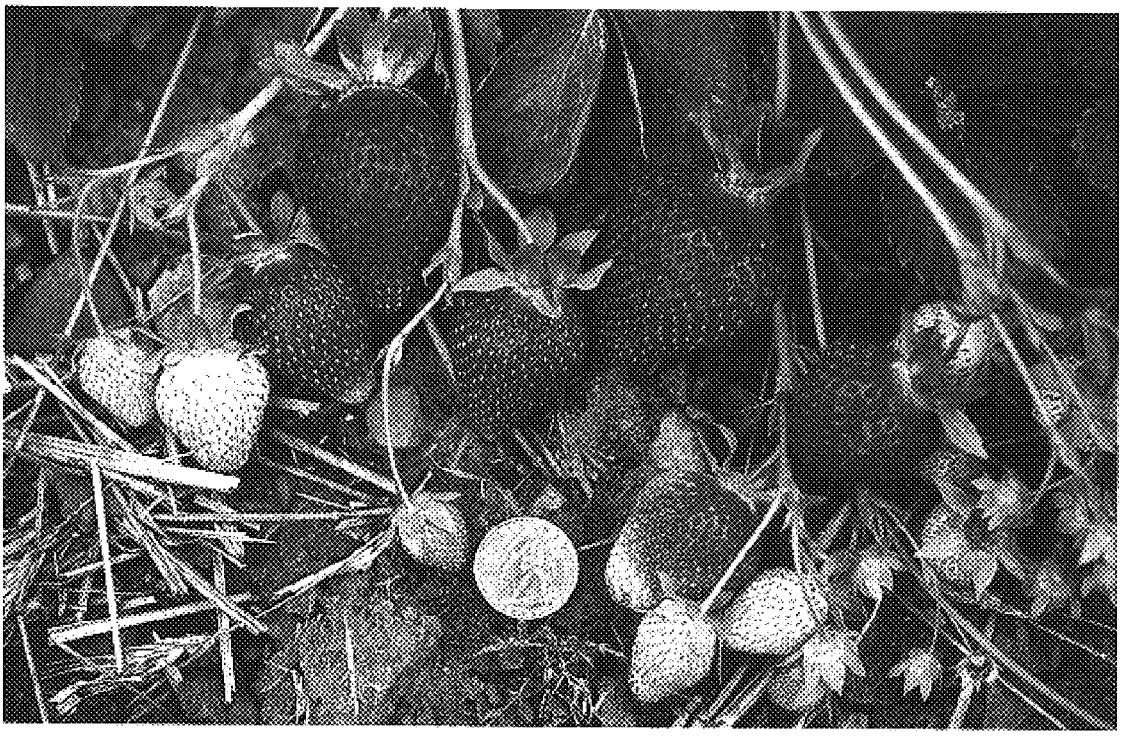
FIG. 1 shows typical fruiting truss of 'L'Amour' on Jun. 20, 2003.
Figure 2:
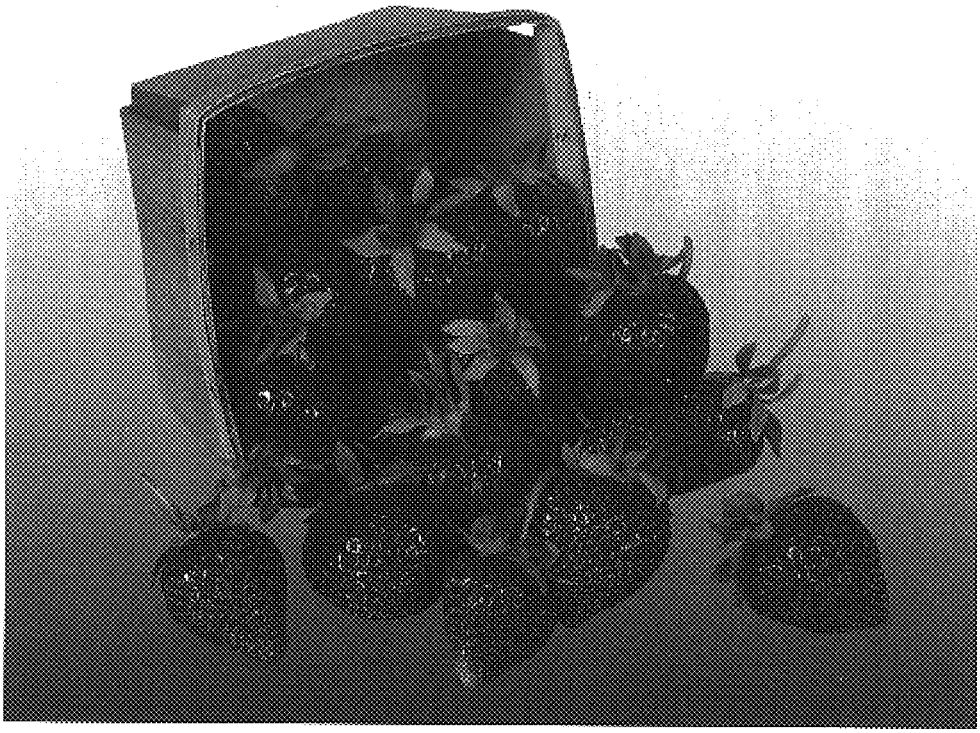
FIG. 2 shows typical fruit shape and uniformity of 'L'Amour'.
Figure 3:
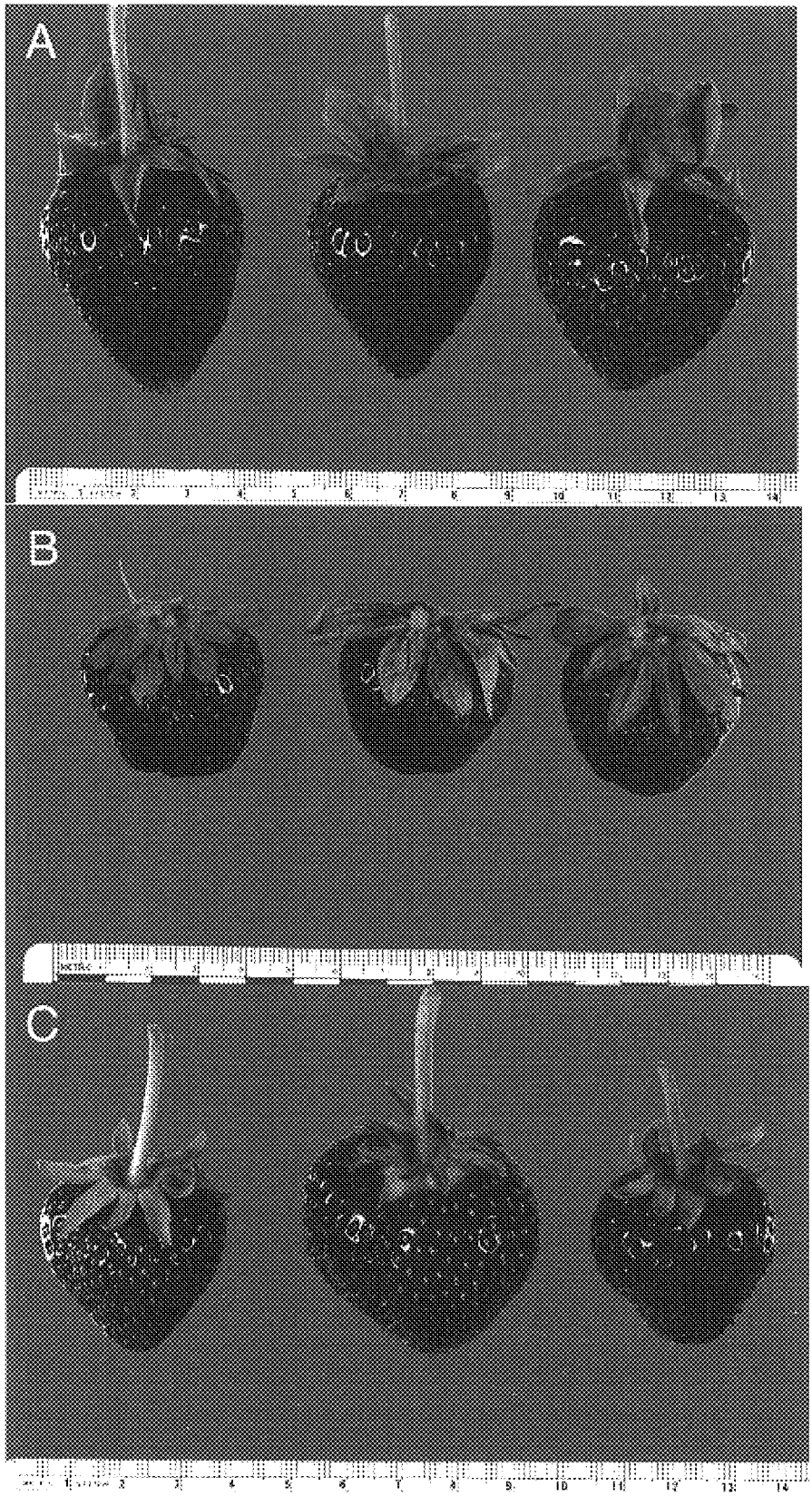
FIG. 3 shows typical external fruit characteristics of 'L'Amour' (A), including calyx structure and fruit shape compared to 'Darselect' (B) and 'Jewel' (C) on Jun. 20, 2003.
Figure 4:
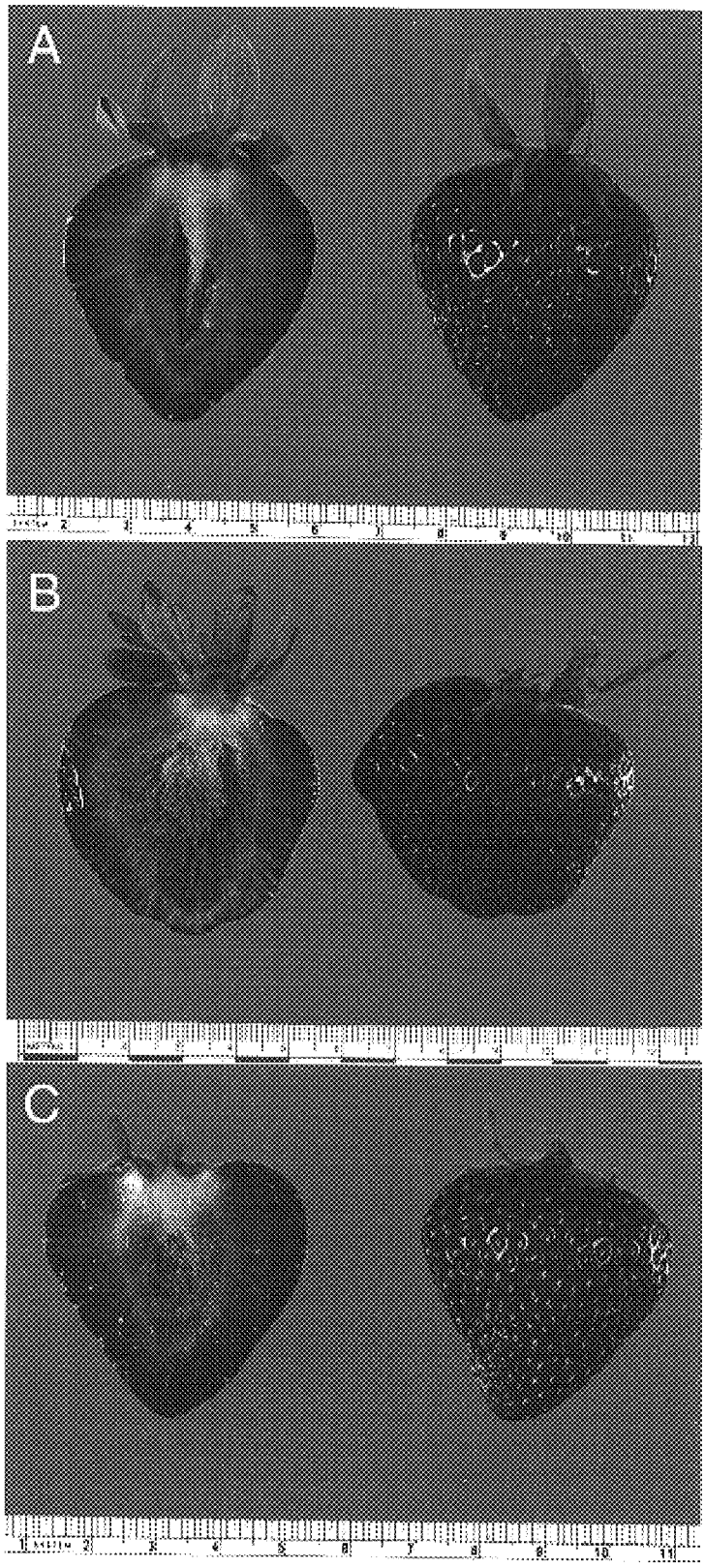
FIG. 4 shows typical internal fruit characteristics of 'L'Amour' (A) compared to 'Darselect' (B) and 'Jewel' (C) on Jun. 20, 2003.

The following description of 'L'Amour' unless otherwise noted, is based on observations taken during the 2003 growing season in Geneva, N.Y. These measurements and ratings were taken from plants produced in South Deerfield, Mass. and planted in May 2001. The age of the planting is approximately 25 months in its second harvest season. Yield observations and fruit quality characteristics are averaged from data collected during the 2002 through 2003 production seasons. The characteristics of the new cultivar may vary in detail, depending upon variations in environmental factors, such as temperature, rainfall, humidity and light intensity. 'L'Amour' has not been observed under all possible environmental conditions. Color terminology where noted follows The Royal Horticultural Society Colour Chart, London.

Comparative fruit characteristics: 'L'Amour' fruit, fruit production and fruit quality characteristics. Fruit characteristics are taken from the second harvest season.

TABLE 1

Table 1 shows the 2002–2003 fruit yield and fruit size of 'L'Amour' from Geneva, NY. Fruit was harvested in June 2002–2003. The plants of 'L'Amour'and the other varieties were grown in a nursery in South Deerfield, MA and planted in May 2001 in Geneva, NY.

| Cultivar | 2002 | 2003 | Average | 2002 | 2003 | Average |
|---|---|---|---|---|---|---|
| | (kilograms per hectare) | | | (grams per berry) | | |
| 'L'Amour' | 15,930 | 14.950 | 15,440 | 12.3 | 11.4 | 11.9 |
| 'Darselect' | 23,530 | 16,120 | 19,830 | 11.5 | 12.0 | 11.8 |
| 'Jewel' | 20,250 | 11,650 | 15,950 | 10.5 | 12.9 | 11.7 |
| 'Honeoye' | 18,280 | 14,470 | 16,375 | 10.7 | 12.4 | 11.6 |

TABLE 2

As shown in Table 2, comparisons of secondary fruit characteristics of 'L'Amour' as compared with standard varieties from Geneva, NY Jun. 20, 2003. Measurements are given for mature fruit. Fruit width is measured across the widest part of the berry, typically across the shoulders.

| Characteristic | L'Amour' | 'Darselect' | 'Jewel' | 'Honeoye' |
|---|---|---|---|---|
| RHS Exterior Color | Red 46B | Red 43A | Red 44A | Red 46A |
| Mature Fruit Length Mean (cm) | 4.22 | 3.45 | 3.46 | 3.85 |
| Mature Fruit Width Mean (cm) | 3.62 | 3.52 | 3.61 | 3.55 |
| Mature Fruit Length/Width Ratio | 1.20 | 1.03 | 1.05 | 1.08 |
| No. Sepals/Berry | 11.0 | 13.7 | 12.4 | 12.7 |

TABLE 3

As shown in Table 3, comparisons of 2003 fruit quality characteristics, including flavor and soluble solids (% Brix), titratable acidity and juice pH of 'L'Amour' are compared with standard varieties from Geneva, NY.

Flesh firmness (fresh) is an average penetration pressure using a Fruit Firmness Tester (QA Supplies, LLC, Norfolk, VA) measured on fruit on the day of harvest with a 3 mm probe following manufacturer's instructions.

Flesh firmness (stored) is an average penetration pressure after 6 days of storage at 2° C. using a Fruit Firmness Tester (QA Supplies, LLC, Norfolk, VA) taken with a 3 mm probe following manufacturer's instructions.

Fruit appearance (fresh) is based on a scale of 1–5 (5 being best) on the day of harvest.

Fruit appearance (stored) is based on a scale of 1–5 (5 being best) after 6 days of storage at 2° C.

Fruit gloss (fresh) is based on a scale of 1–5 (5 being best) on the day of harvest.

Fruit gloss (stored) is based on a scale of 1–5 (5 being best) after 6 days of storage at 2° C.

Flavor is based on a scale of 1–10 (10 being best) rated on day of harvest by a panel of tasters.

Soluble solids are estimated from % Brix with % Brix being an indirect measurement of the sugar content in the fruit. The measurements are averaged from three samples on three dates during the harvest season.

Titratable acidity is the percent of malic acid equivalents. The figures shown are the average of three samples on three dates during the harvest season.

Juice pH is the average of three samples on three dates during the harvest season.

| Characteristic | 'L'Amour' | 'Darselect' | 'Jewel' | 'Honeoye' |
|---|---|---|---|---|
| Flesh firmness (fresh) (g pressure) | 268.3 | 173.3 | 145.3 | 149.7 |
| Flesh firmness (stored) (g pressure) | 248.3 | 160.0 | 141.7 | 139.0 |
| Fruit appearance (fresh) | 5.0 | 3.5 | 4.7 | 4.0 |

TABLE 3-continued

| | | | | |
|---|---|---|---|---|
| Fruit appearance (stored) | 4.0 | 2.5 | 4.0 | 3.0 |
| Fruit gloss (fresh) | 4.7 | 3.5 | 5.0 | 3.7 |
| Fruit gloss (stored) | 4.0 | 2.5 | 4.3 | 2.3 |
| Flavor | 6.5 | 6.3 | 6.7 | 6.0 |
| Soluble solids | 8.9 | 8.6 | 7.8 | 7.4 |
| Titratable acidity | 1.0 | 0.89 | 1.12 | 1.18 |
| Juice pH | 3.68 | 3.64 | 3.42 | 3.41 |

Detailed fruit characteristics of 'L'Amour':

*Ratio of length/width.*—Longer than broad.

*Size.*—Medium to large.

*Aroma.*—Moderate to high.

*Predominant shape.*—Conical.

*Difference in shapes between primary and secondary fruit.*—Little to none.

*Band without achenes.*—Intermediate width.

*Color of mature fruit.*—Bright to dark red.

*Evenness of color.*—Very even.

*Glossiness.*—Strong.

*Insertion of achenes.*—Level to slightly recessed from surface.

*Attitude of the calyx segments.*—Highly reflexed.

*Color of calyx.*—RHS 143A (green).

*Size of calyx in relation to fruit diameter.*—Generally larger.

*Adherence of calyx (when fully ripe).*—Strong.

*Firmness of skin.*—Strong.

*Firmness of flesh.*—Very firm.

*Color of flesh.*—Medium red with lighter ring (red 43A to 44A).

*Distribution of red color of the flesh.*—Marginal through central with light inner ring.

*Hollow center.*—Weakly to strongly expressed.

*Seed color.*—Medium yellow-green to dark red (yellow-green 151C to red 46B).

*Time of flowering (50% of plants at first flower).*—Medium to early.

*Time of ripening (50% of plants with first ripe fruit).*—Medium to early.

*Type of bearing.*—Fully short day responsive.

Comparative Plant Characteristics:

TABLE 4

Table 4 shows a comparison of plant characteristics of 'L'Amour' along with other standard varieties from Geneva, NY Jun. 20, 2003. Plant characteristics are taken from a fully mature, mid-season plant. Vigor and Canopy Density are rated on a scale of 1–9 (9 being more vigorous or dense) in mature, replicated plots.

| Characteristic | 'L'Amour' | 'Darselect' | 'Jewel' |
|---|---|---|---|
| Plant Height Mean (cm) | 31.9 | 30.0 | 27.3 |
| Vigor | 8.3 | 8.0 | 5.0 |
| Canopy Density | 7.7 | 7.3 | 7.3 |

Detailed plant characteristics of 'L'Amour':

*Size.*—Large.

*Habit.*—Upright.

*Density.*—High.

*Vigor.*—Strong.

*Spread.*—32.4 cm.

Comparative Foliage Characteristics:

TABLE 5

Table 5 shows a comparison of leaf characteristics of 'L'Amour', with standard varieties from Geneva, NY on Jun. 20, 2003. Foliage characteristics are taken from a fully mature tri-foliate leaf during mid-season.

| Characteristic | 'L'Amour' | 'Darselect | 'Jewel' |
|---|---|---|---|
| RHS Color (upper surface) | Green 137A | Green 137B | Green 138A |
| RHS Color (upper surface) | Green 139C | Green 139C | Green 137D |
| Terminal Leaflet Length Mean (cm) | 8.4 | 9.5 | 7.5 |
| Terminal Leaflet Width Mean (cm) | 8.5 | 8.2 | 7.6 |
| Terminal Leaflet Length/Width Ratio | 0.99 | 1.17 | 0.99 |
| Petiole Length Mean (cm) | 22.8 | 22.1 | 19.9 |
| Serrations/Leaf | 22.3 | 19.2 | 18.3 |
| Stipule Length Mean (cm) | 3.5 | 4.6 | 3.0 |
| Stipule Width Mean (cm) | 0.8 | 1.0 | 0.8 |

Detailed foliage characteristics of 'L'Amour':

*Color of upper surface.*—Medium to dark green.

*Color of lower surface.*—Medium to light green.

*Shape in cross section.*—Slightly concave.

*Interveinal blistering.*—Light to moderate.

*Glossiness.*—Moderate.

*Number of leaflets/leaf.*—Three.

*Terminal leaflet.*—Size — Medium. Length/width ratio — Equally long as broad. Shape of base — Cuneate. Shape serrations — Mucronate.

*Petiole.*—Pubescence density — Moderate to high. Color — RHS 145B (yellow-green). Stipule color — Light to medium green (green 151A). Stipule texture — Surface is moderately pubescent. Anthocyanin coloration of stipule — Little to none. Attitude of hairs — Strongly outward. Size of bract leaflets — Small. Frequency of bract leaflets — Occur on approximately 10% of the petioles.

Comparative Flower and Inflorescence Characteristics:

TABLE 6

Table 6 gives a comparison of inflorescence and secondary flower characteristics of 'L'Amour' as compared with standard varieties from Geneva, NY on May 20, 2003.
The fruiting truss length is measured from the base of the primary peduncle where it attaches to the crown of the plant to the furthest berry.

| Characteristic | 'L'Amour' | 'Darselect' | 'Jewel' |
|---|---|---|---|
| Fruiting Truss Length Mean (cm) | 32.3 | 28.8 | 20.9 |
| Corolla Diameter Mean (mm) | 36 | 31 | 31 |
| Calyx Diameter Mean (mm) | 33 | 38 | 34 |
| Petal Length Mean (mm) | 15.4 | 14.6 | 14.0 |
| Petal Width Mean (mm) | 13.6 | 14.3 | 13.3 |
| Petal Length/Width Ratio | 1.13 | 1.02 | 1.09 |
| Petals/Flower Mean | 5.1 | 6.1 | 6.3 |
| Sepals/Flower Mean | 11.0 | 13.7 | 12.4 |

Detailed inflorescence characteristics of 'L'Amour':

*Position relative to foliage.*—Above.

*Fruiting truss length.*—Long.

Detailed flower characteristics of 'L'Amour':

*Color.*—RHS 155C (white).

*Size.*—Medium to large.

*Size of calyx relative to corolla.*—Smaller.

*Relative position of petals.*—Little to no overlap.

*Petal length/width ratio.*—Longer than broad.

*Petal shape.*—Nearly round.

Pest reactions: It is known to be moderately resistant to the two-spotted spider mite and susceptible to aphid and flower thrips. It is also known to be moderately resistant to grey fruit mold and slightly susceptible to powdery mildew. The susceptibility of the new cultivar to any of the virus complexes of NY has not been determined.

COMPARISON WITH KNOWN VARIETIES

'L'Amour' is distinguished from its parents by having larger fruit, firmer fruit flesh, and ripening later than NYUS256. The plant vigor of 'L'Amour' is greater than NYUS256 in that it is taller and fills the plot more fully. It is distinguished from 'Cavendish' in that the fruit of 'L'Amour' have more even ripening in hot weather, has larger fruit on average, is lighter red in color, and is firmer with better storage capacity.

The varieties which are believed to most closely resemble 'L'Amour' are 'Honeoye' (not patented), 'Darselect' (U.S. Plant Pat. No. 10,402) and 'Jewel' (U.S. Plant Pat. No. 5,897).

When compared to the similar cultivar 'Honeoye', 'L'Amour' differs by the following characteristics. The plant of 'L'Amour' is taller and more upright in growth habit with greater vigor. The fruit of 'L'Amour' is larger than that of 'Honeoye'. The fruit skin and flesh color of 'L'Amour' is lighter red than that of 'Honeoye'. The yield of 'L'Amour' is less than that of 'Honeoye'. The fruit of 'L'Amour' is firmer with glossier skin than that of 'Honeoye'. The fruit of 'L'Amour' has higher soluble solids (% Brix) and lower titratable acids than that of 'Honeoye' with higher juice pH. The calyx of 'L'Amour' is showier, larger and more reflexed than that of 'Honeoye'. The harvest season of 'L'Amour' is later than that of 'Honeoye' and slightly less compact.

When compared to the similar cultivar, 'Darselect', 'L'Amour' differs by the following combination of characteristics. The plant of 'L'Amour' is slightly taller and more upright in growth habit compared to 'Darselect' with greater vigor. The leaflets are wider and shorter, being more globose in shape with slightly less interveinal leaf blistering. The length to width ratio of the terminal leaflet is equally long and broad compared to much longer than broad for 'Darselect'. The stipules of 'L'Amour' are shorter than those of 'Darselect'. The fruit of 'L'Amour' is slightly larger in size, with darker red skin and flesh color than 'Darselect'. The fruit of 'L'Amour' is firmer with glossier skin than 'Darselect'. The fruit of 'L'Amour' has higher average soluble solids and lower juice pH. The difference in shape between primary and secondary fruit is greater in 'Darselect' than 'L'Amour'. The flowering trusses of 'L'Amour' are longer and have more flowers than 'Darselect'. The flowers of 'L'Amour' are larger in diameter than the flowers of 'Darselect' with petals that are longer than wide compared to equally long and wide in 'Darselect'. The harvest season for 'L'Amour' is more compact than that of 'Darselect'.

When compared to the similar cultivar, 'Jewel', 'L'Amour' differs by the following combination of characteristics. The plant of 'L'Amour' is more vigorous with a taller, more upright habit and thicker canopy when compared to 'Jewel'. The foliage is larger in size with more interveinal leaf blistering. A single petiole bract is occasionally present in 'L'Amour' and absent in 'Jewel'. The stipules of 'L'Amour' are longer than those of 'Jewel'.

The fruit of 'L'Amour' is larger in size, darker in color than 'Jewel'. The calyx segments are highly reflexed in 'L'Amour' compared to flush with the fruit in 'Jewel'. The fruiting trusses of 'L'Amour' are longer in overall length than 'Jewel' with more flowers per truss. The fruit of 'L'Amour' has much higher soluble solids, lower titratable acidity than that of 'Jewel' with a higher juice pH.

We claim:

1. A new and distinct cultivar of strawberry plant named 'L'Amour' substantially as herein described and illustrated by the characteristics set forth above.

* * * * *